US00RE39301E

(19) United States
(12) Reissued Patent
Bertin

(10) Patent Number: US RE39,301 E
(45) Date of Reissued Patent: Sep. 19, 2006

(54) METHOD FOR RESECTING THE KNEE USING A RESECTION GUIDE AND PROVISIONAL PROSTHETIC COMPONENT

(75) Inventor: Kim C. Bertin, Salt Lake City, UT (US)

(73) Assignee: Zimmer, Inc., Warsaw, IN (US)

(21) Appl. No.: 08/698,781

(22) Filed: Aug. 16, 1996

Related U.S. Patent Documents

Reissue of:
(64) Patent No.: 5,458,645
Issued: Oct. 17, 1995
Appl. No.: 08/021,039
Filed: Feb. 23, 1993

U.S. Applications:
(62) Division of application No. 07/862,953, filed on Apr. 3, 1992, now Pat. No. 5,258,032.

(51) Int. Cl.
*A61B 17/00* (2006.01)
*A61B 19/00* (2006.01)
*A61F 2/38* (2006.01)

(52) U.S. Cl. ..... 606/88; 623/20.14; 128/898; 606/86

(58) Field of Classification Search ..... 623/16, 623/18, 20, 66; 606/80, 86, 87, 88, 89
See application file for complete search history.

(56) References Cited

U.S. PATENT DOCUMENTS 4,502,483 A 3/1985 Lacey
4,524,766 A 6/1985 Petersen
4,646,729 A 3/1987 Kenna et al.
4,721,104 A * 1/1988 Kaufman et al. ..... 606/88
4,759,350 A 7/1988 Dunn et al.
5,053,037 A * 10/1991 Lackey ..... 606/88
5,100,409 A * 3/1992 Coates et al. ..... 606/88
5,250,050 A * 10/1993 Poggie et al. ..... 606/88
5,282,803 A * 2/1994 Lackey ..... 606/88

FOREIGN PATENT DOCUMENTS

EP 0121786 10/1984

* cited by examiner

*Primary Examiner*—David Isabella
(74) *Attorney, Agent, or Firm*—M. Reid Russell

(57) ABSTRACT

A method and apparatus for knee replacement surgery wherein a femoral provisional component is provided which corresponds to a permanent component to be implanted in a human and which includes means for establishing the correct fit and position of such a component, prior to its implantation, in relation to the soft tissues of the knee before final resection of the anterior femoral surface. The provisional component further includes cutting guide means for such anterior surface resection such that accurate cuts may be made with the provisional component in place. The method involves preparing the distal femoral surface using the femoral intramedullary canal as a constant reference point for posterior and distal cutting guides followed by locating the provisional component by means of a provisional intramedullary stem so that the relationship with the soft tissues of the knee may be accurately established.

18 Claims, 3 Drawing Sheets

METHOD FOR RESECTING THE KNEE USING A RESECTION GUIDE AND PROVISIONAL PROSTHETIC COMPONENT

Matter enclosed in heavy brackets [ ] appears in the original patent but forms no part of this reissue specification; matter printed in italics indicates the additions made by reissue.

[This is a division of application Ser. No. 07/862,953 filed Apr. 3, 1992 now abandoned.] *This application is a reissue of application Ser. No. 08/021,039, now U.S. Pat. No. 5,458,645, which is a divisional of application Ser. No. 07/862,953, filed Apr. 3, 1992, now U.S. Pat. No. 5,258,032.*

FIELD OF THE INVENTION

The present invention relates to a method and apparatus for a knee joint prosthes is and surgical procedure. More particularly concerning the proper fitting of the femoral component of a total knee revision prosthesis, the procedure for performing revision surgery and apparatus used therein.

BACKGROUND OF THE INVENTION

The present invention relates to a provisional knee prosthesis and resection guide component together with a surgical procedure designed for use as a system in revision surgery of previously performed knee arthroplasties. It may also find utility in an initial knee replacement procedure.

Revision surgery is performed to correct failures of previously implanted knee prostheses. These failures occur for a number of reasons including malposition, loosening of the prosthesis, infection or dislocation. Such categories are not necessarily mutually exclusive since infection may cause a loosening of the prosthesis which, in turn, might cause dislocation.

When a prosthesis must be removed and a revision prosthesis inserted, it is often the case that additional bone must be removed in order to stabilize the new prosthesis. When this occurs, the interior portion of the femoral component of the prosthesis must be augmented to add additional thickness to compensate for the bone that has been removed. In addition, the revision cuts that remove the extra bone must be made correctly relative to the revision prosthesis for accurate positioning in relation to a tibial component and the soft tissues of the knee joint. Such cuts are made with the aid of guides positioned relative to the ends of the femur and tibia.

It is preferable to perform revision in a single surgical procedure. Also, it is desirable to be able to test the fit and operation of the prosthesis relative to the rest of the knee, particularly the patella and the soft tissues, prior to or at the same time as the revision cuts are made in the end of the femur. Indeed, with regard to patellar tracking, it is preferable to ensure a proper fit before the final anterior cuts are made to the distal femur.

The apparatus and method of this invention are intended to be used in conjunction with the revision prosthesis system of applicant's co-pending application which is based around a constant geometry of the anterior flange, the distal prosthesis and the intramedullary stem of the component and uses the intramedullary canal of the femur as a reference point. Accordingly, the present invention is similarly based around the intramedullary canal of the femur as a reference point for all of the bone cuts.

DESCRIPTION OF THE PRIOR ART

Tibial resection for implantation of the tibial component of an initial knee prosthesis or revision is relatively straightforward as it essentially only requires surface treatment of the proximal end of the tibia. In such treatments, cutting guides are normally positioned relative to the intramedullary canal of the tibia by attaching the guides to the intramedullary reamer or to an alignment rod placed within the reamed canal. Such devices are shown in U.S. Pat. Nos. 4,952,213 to Bowman, et al., and 5,002,545 to Whiteside, et al.

In contract, however, prior apparatus and methods for performing the comparable resection of the distal femur have included both intramedullary and extramedullary positionable guide means, often both, frequently requiring accurate adjustment for the individual circumstances. The intramedullary positioned guide means have been traditionally used only for the distal and posterior resection of the femur leaving the anterior cuts to be made with extramedullary positioned means.

Such intramedullary positionable distal and posterior cut guide means are represented by U.S. Pat. Nos. 4,703,751 to Pohl and 4,935,023 to Whiteside, et al. The Pohl patent presents a guide means for resection of the distal surface, which guide is positionable on a jig which is removably connected to an intramedullary rod. The jig allows the cutting guide to be angularly pivoted relative to the center line of the femur. Whiteside, et al., present a shaping guide also removably attachable to an intramedullary rod and having an adjustable positioning means together with guides for the shaping of only one condyle in preparation for the implantation of a unicondylar prosthesis.

It is known for anterior surface resection guides to be positionable relative to an intramedullary rod, for example U.S. Pat. No. 4,474,177 to Whiteside presents an apparatus for shaping the distal femoral surface wherein a plurality of shaping instruments or guides are selectively positionable on an intramedullary rod for use in guiding a saw blade during the procedure. However, what the prior art lacks is an apparatus and method whereby all cuts can be made from the common reference point of the intramedullary canal of the femur and whereby the positioning and size of a femoral component may be checked relative to the soft tissues and the track of the patella prior to making the final resection of the anterior surfaces. In the case of Whiteside, the cuts are made first then the guides are removed before any test fittings can be conducted. If the cuts are made in the wrong place or to the wrong degree, then the surfaces must be modified by further resection, bone grafts or bone cement to get a proper fit of the implant.

SUMMARY OF THE INVENTION

The present invention provides a provisional component which allows the selected size of a prospective implant to be test fit with respect to the distal and posterior resections of the femur and the soft tissues of the knee joint before making the final resection of the anterior surface of the femur. It also provides a guide means as an integral part of the provisional component for making those final cuts to the anterior surface. Furthermore, it provides a means whereby the relative spacing of the extension and flexion gaps in the knee joint may be tested using the provisional component with prospective augments or trial pieces, when necessary, in place following which the provisional component itself serves as the guide for making the final surface cuts thus ensuring that the resected femur and ultimate permanent prosthesis will result in a properly balanced knee.

The augments, which are modular and therefore independently changeable, allow adjustment of the anterior/ posterior box size as well as the distal positioning of the provisional component. Such distal positioning is crucial for obtaining correct soft tissue balance in the knee during trial reduction before final anterior resection and implantation of the permanent prosthesis. Modular augments and pretesting of the knee with the provisional component of the present invention also enable the surgeon to ensure a close contact fit of the prosthesis with the resected bone surface whereby a greater degree of adhesion may be obtained through bone ingrowth or less bone cement need be used.

The provisional component is constructed to emulate the permanent implant while being temporarily placed in the joint space. Such a permanent implant system is described by my copending application Ser. No. 07/862,954 filed Apr. 3, 1992. It includes the anterior and posterior condylar flanges as well as the intermediate distal portion of the joint surface. An intramedullary stem is provided or, alternatively, the provisional may be adapted for attachment to an intramedullary rod or reamer placed in the femoral intramedullary canal. Provision is also made for the provisional component to temporarily accept distal and posterior augments for proper spacing so that the final anterior surface cuts will be accurately made. With regard to those cuts, the provisional component includes bone saw guides positioned through the body of the component relative to the anterior flange for the correct location and angular position of the chamfer and anterior surface cuts necessary to fit a final permanent implant.

It is therefor an object of this invention to provide a combination knee prosthesis provisional apparatus and resection guide for use in knee replacement surgery whereby resection and test fitting of femoral prostheses may be easily and reliably achieved.

It is a further object of this invention to provide a means whereby the spacing of extension and flexion gaps of the knee may be tested and evaluated during the process of replacement surgery prior to final resection and prosthesis implantation.

It is a still further object to provide a means whereby the resection of the distal femur is made on the basis of a reference point common to all resection cuts slid implant sizes.

It is an even further object to provide a combination knee prosthesis provisional apparatus and resection guide which emulates a permanent femoral implant component.

Further objects and advantages will become evident to those of skill in the art from the following drawings and description.

DETAILED DESCRIPTION OF THE INVENTION

Figure 1:
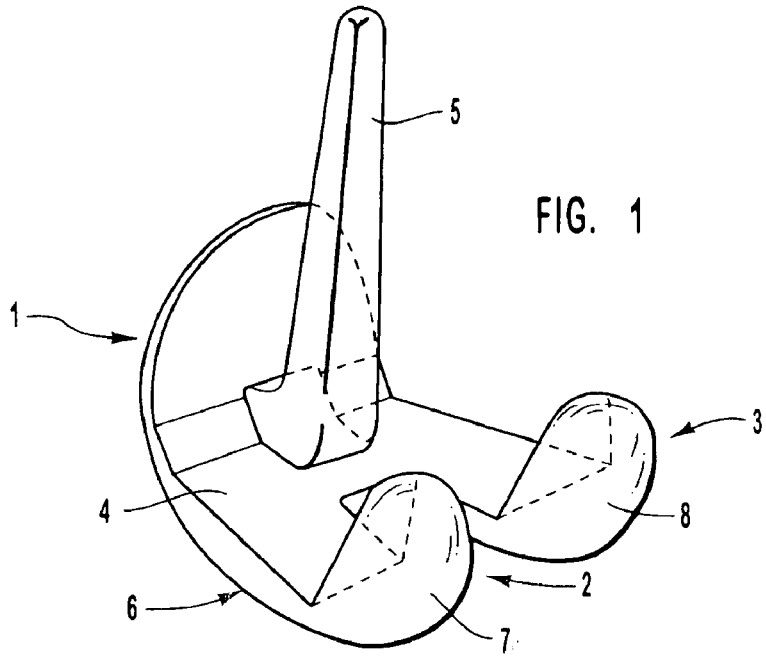
FIG. 1 is an oblique view of a standard femoral component of a knee revision prosthesis.

The femoral component revision prosthesis of FIG. 1 is similar to that employed in most knee prosthetics in that it comprises an anterior flange 1, a pair of posterior condylar flanges 2 and 3, a distal femur contacting surface 4, an intramedullary locating and anchor shaft 5 and a distal joint surface 6 corresponding to the natural distal femoral surface of the human knee with condylar surfaces 7 and 8 for cooperation with the corresponding end of a tibia and means for patellar tracking along the arc of the joint surface of the anterior flange 1 and between the distal condylar surfaces 7 and 8. Femoral component prostheses of this general type have been used for some time in knee reconstruction and have been made available in a range of sizes to accommodate patients having different skeletal and joint sizes. Such components have required that the distal end of the femur be resected to the specific size of the individual component, necessitating careful shaving of the bone by the surgeon and multiple fittings of the prosthesis before the procedure is finished. Alternatively, a wide array of augments attachable to the distal femur contacting surface 4 of the component have been necessary to ensure a proper fit of the correct size component to a patient's femur.

For an initial femoral implant, it is generally not as difficult to obtain a correct fit of the proper size component; although the problem can occur where there is a great deal of diseased bone that must be removed before the implant is fitted. Such instances then become similar to those encountered in revision surgery where it is necessary to remove existing bone along with the original implant either due to infection or physical breakdown of the previously prepared distal femur. In these cases the size of the bone supporting the implant is reduced but it is still desired to maintain the size of the original joint in order to obtain proper anatomical characteristics of support and function for the patient. For example, a patient having an anatomical knee size of six may, following resection of the femur, have a distal femoral surface corresponding to that for a size four and a half knee. In order to maintain the proper anatomical characteristics for that knee it is desirable that the implanted component be a size six. However, adapting a larger size implant to a smaller size bone has presented difficulties which, to date, have been solved by the use of custom made implants or multiple augments.

Prior devices and methods have required measuring the size of the bone and then cutting it to fit one specific size of prosthesis. This allows a good fit to be obtained between the prosthesis and the bone but may not provide a good fit with the soft tissues and the patella. In revision surgery, the flexion space of the knee, ie., that space between the posterior edge of the prepared distal femur and the prepared proximal tibia when the knee is fully bent as shown by space B in FIG. 3, is often greater than the extension space, ie., that space between the distal femur and proximal tibia when the knee is fully extended, as shown by space A in FIG. 2. For proper working of the knee joint the tension between the distal femur and the proximal tibia should be the same whether the knee is in flexion or extension. However, it is often the case in revision surgery that resection of the distal femur is uneven resulting in irregularities in the spacing of the flexion and extension gaps which, in turn, produces uneven tension across the knee. The present apparatus and method allow testing of the knee action with the provisional component, which corresponds to the permanent implant, in order to ensure that the flexion and extension gaps are even for proper working of the knee before final resection cuts are made to the anterior surface of the femur and to ensure a close contact fit with the resected bone surface. The femoral components of applicant's copending application and the method and apparatus of this invention are based around the intramedullary canal as a constant point of reference as well as a constant geometry of the components in a set with regard to the relationship between the intramedullary stem and the anterior flange of the components. This makes adjustment and placement of femoral components during surgery easier since it eliminates at least one variable from the procedure. Since the relationship between the intramedullary stem and the anterior flange is constant, the anterior resection cuts must be properly placed relative to the intramedullary canal as well as relative to the posterior and distal cuts in order to obtain a properly workable knee joint. The apparatus and method of this invention provide the means whereby this is achieved.

Figure 2:
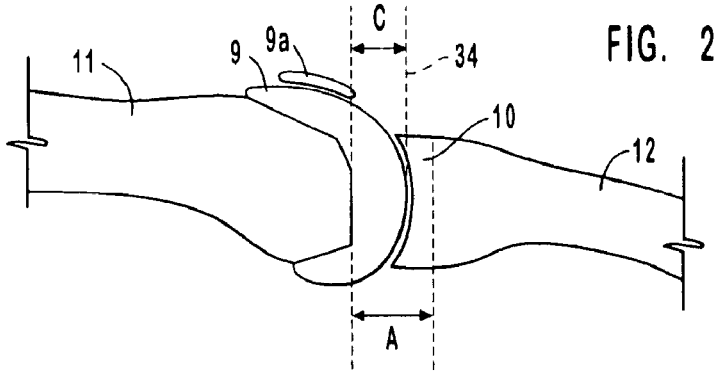
FIG. 2 is a view of a knee joint in full extension.
Figure 3:
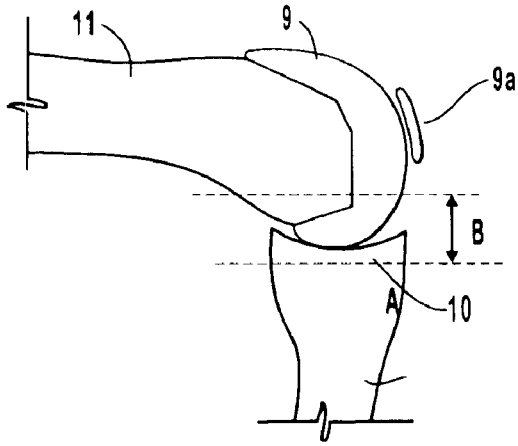
FIG. 3 is a view of a knee joint in full flexion.

FIGS. 2 and 3 illustrate the relationships of femoral 9 and tibial 10 components in a knee joint at full extension and full flexion respectively. Under optimum conditions, the extension gap A and the flexion gap B should be equal for a properly functioning and stable knee. This relationship between the femur 11 and tibia 12 is important to get the knee implant components to interface properly with the soft tissues of the joint and to achieve a proper soft tissue balance within the knee. The size of the femoral revision component usually increases relative to the centerline through the fixation stem 5 with the posterior portion 6 being increased to tighten the flexion space B. However, this often affects the other relationships within the knee and upsets the soft tissue balance. In the present invention the distal and posterior adjustments are made with the addition of augments between the femoral component 9 and the respective cuts made to the femur 11. Furthermore, since the inventions herein and in applicant's copending application are based around the intramedullary canal and the anterior flange as constants, it is important that the anterior resection be identical and properly placed. Accordingly, the provisional component of FIG. 4 provides a means whereby the knee joint may be tested for proper fit and function prior to resection of the anterior femur and whereby that resection may be accomplished while the provisional component is in place, thereby ensuring that the anterior cuts are made in the correct place relative to all other aspects of the joint replacement components.

Figure 4:
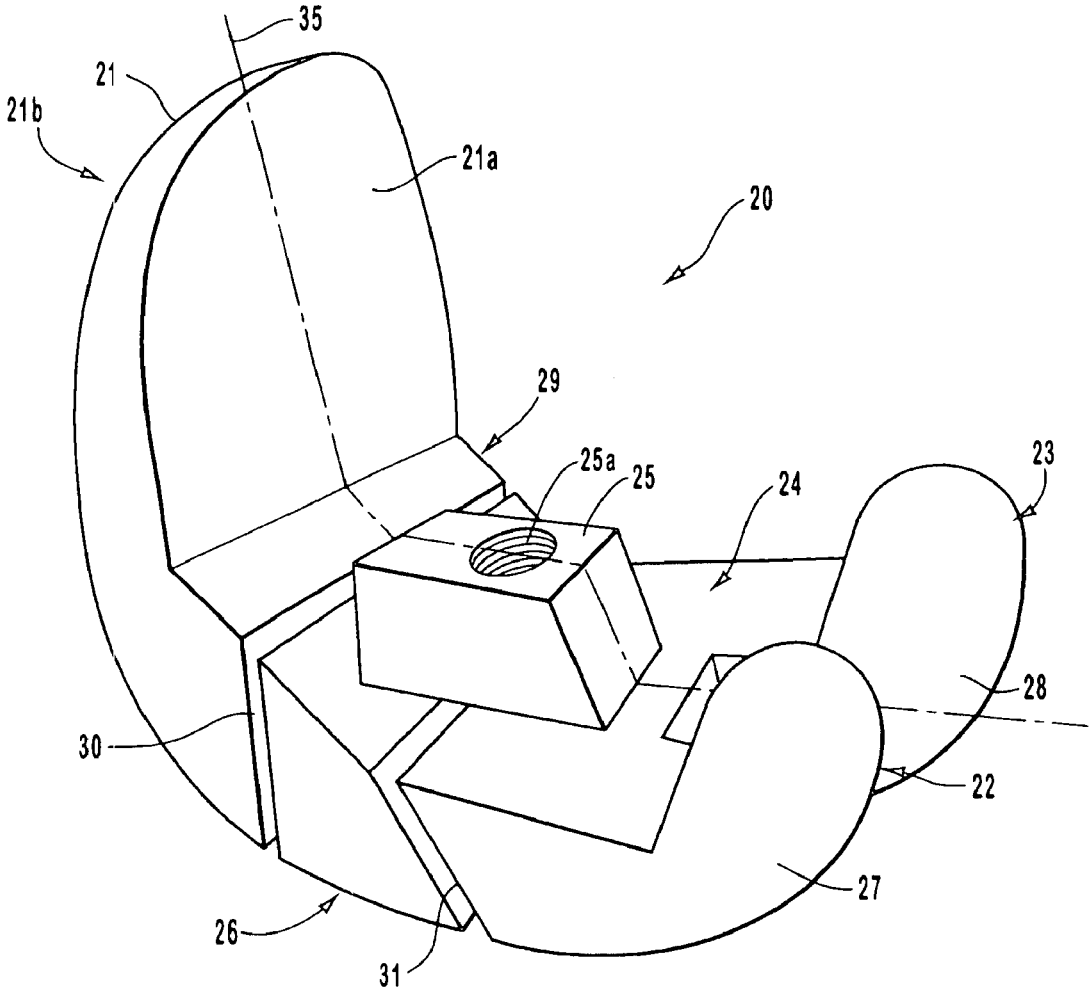
FIG. 4 is an oblique view of the femoral component provisional and resection guide apparatus of the present invention.
Figure 7:
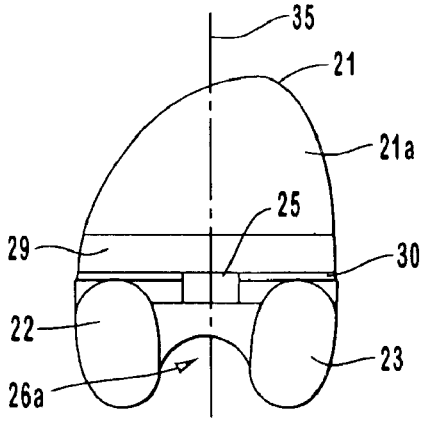
FIG. 7 is a posterior elevation view of the femoral component provisional and resection guide apparatus of FIG. 4.

FIGS. 4 and 7 illustrate the combination femoral provisional component and anterior resection guide 20 of the invention which comprises a femoral component similar to that shown in FIG. 1. The provisional 20 comprises an anterior flange 21, posterior condylar flanges 22 and 23, a distal femur contacting surface 24 and a distal joint surface 26 which corresponds to the natural distal femoral surface of the human knee with condylar surfaces 27 and 28. Between the distal femur contacting surface 24 and the inner surface 21a of anterior flange 21 is chamfer 29 which will correspond to a chamfer cut made to the distal femur during resection procedures to be described later. Located medially on the distal femur contacting surface 24 adjacent chamfer 29 is the fixation point 25 for an intramedullary stem, rod or reamer by which the provisional component 20 is affixed to a femur in proper relation to the intramedullary canal reference point. Any suitable means for connection of the intramedullary location means may be used such as threads, 25a as shown, press fit, detents, or the like.

The provisional component of this invention, as well as the revision prosthesis of applicant's co-pending application, have a constant relationship between the center line of the stem, or stem fixation point, and the anterior cornea of the femur for all sizes of the component. This relationship provides a constant angle between the stem and the cortex, represented by the inner surface of the anterior flange, as well as a fixed distance therebetween which is the same regardless of the anatomical sizes of the provisional components to be available in a system.

The joint surface 26 is continuous and extends around the outer periphery of the component 20 to include the outer surface 21b of the anterior flange 21 as well as the outer surfaces of the posterior condylar flanges 22 and 23 and the distal femoral joint portion. Similarly, inasmuch as the component emulates the joint surface of a natural distal femur, the condylar surfaces 27 and 28 continue around the periphery of the component as part of the joint surface 26 thereby providing distal, medial and lateral condylar surfaces between which will be located a track area or groove 26a for travel of the patella as the knee joint flexes. Such travel is shown in FIGS. 2 and 3 by the relative positions of the patella 9a. This structure of the provisional component enables it to be placed in the joint space following resection of the distal and posterior femur. Preferably, the resection of the posterior and distal surfaces of the medial and lateral condyles is kept to the least amount necessary. In addition, each condyle is preferably resected independently of the other and separate augments are selected for test fitting the provisional component and for final implantation of the a femoral implant component. These cuts may be standardized relative to the anatomical characteristics of an average range of knee sizes for a population or they may be made on the basis of each individual case. The function of the knee may then be checked as well as the relationship of the provisional to the soft tissues of the joint. Although the correct size provisional component and, thereby, the prosthesis will usually be determined before surgery, it may be necessary, following initial resection, to upsize to the next larger component in order to tighten the flexion and extension gaps. The present invention facilitates this process by permitting the sizes to be tested before the final prosthesis is implanted. Once correct working of the joint is established, including balancing of the soft tissues, the anterior chamfer and anterior flange resection may be accomplished without removing the provisional component thereby ensuring that these cuts are made in the correct locations relative to the intramedullary canal and at the correct angles relative to the intramedullary stem.

It is important that the anterior flange cut be made last, after the posterior and distal cuts and after correct working of the joint and soft tissue balance has been established. Because the system of revision for which the provisional component of this invention is intended uses the intramedullary canal of the femur as a reference point, the angle established between a reamer or intramedullary shaft and the anterior flange of an implant is constant through all sizes of such implants. Therefore, if the anterior flange cut is made before the posterior and distal cuts and before the extension and flexion gaps are stabilized, the constant relationship will be lost once those cuts are made and stabilization of the knee and soft tissue balance will be much more difficult to achieve. Thus, the correct order for the procedure is to first resect the distal and posterior femoral surfaces with the cutting guides therefor positioned relative to the reamer used to prepare the intramedullary canal. Following this, the provisional component is inserted, using either the reamer or a separate intramedullary shaft for positioning, and the fit and balance of the knee are determined before finally making the anterior flange cuts.

To accomplish this, the provisional component 20 is provided with cutting guides 30 and 31. These guides 30 and 31 comprise slots in the body of the provisional component 20 with guide 30 at the correct angle and location for the anterior flange resection cut while guide 31 is at the correct angle and location for the anterior chamfer resection cut. Each guide actually comprises two slots placed on either side of the intramedullary stem fixation point 25 and extending from the edge of the component 20 inward toward the longitudinal center line 35 of the component to a point adjacent the intramedullary stem fixation point 25. The slots further extend completely through the component 20 from the joint surface 26 to the femoral contact surface 24 with the two slots of each guide 30 and 31 being necessarily located on the same relative plane through the component 20. Clearly, cutting guides 30 and 31 do not extend completely across component 20 from edge to edge in order to maintain the component as a complete unit. Also, the cutting is primarily conducted on the condylar surfaces of the femur which will provide a guide for any final dressing of the intervening mid surface.

Figure 5:
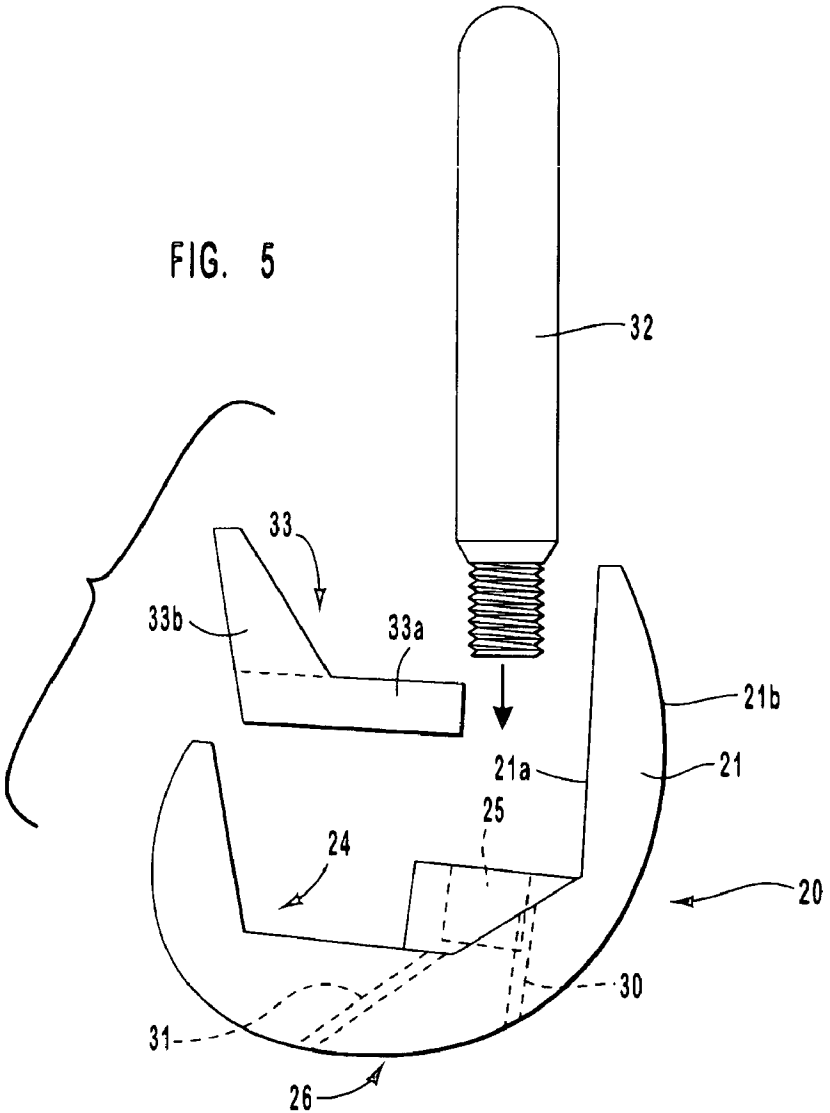
FIG. 5 is a composite view of the femoral component provisional and resection guide apparatus of the present invention illustrating its component parts.
Figure 6:
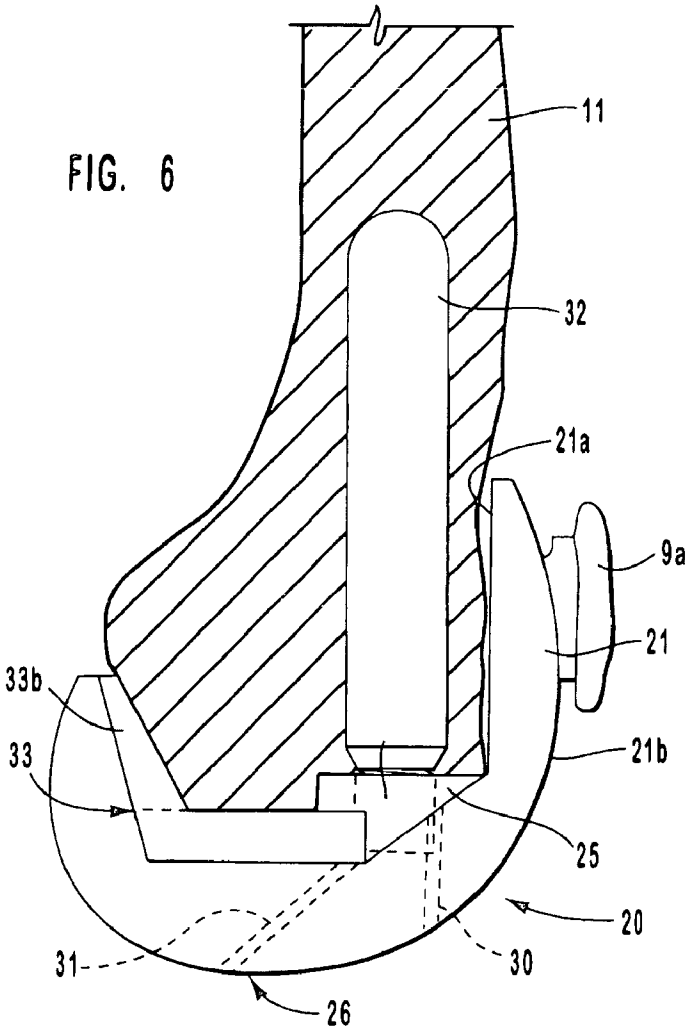
FIG. 6 is a cross section of a partially prepared femur illustrating the femoral component provisional and resection guide in place prior to making anterior flange and chamfer cuts on the femur.

FIG. 5 illustrates the primary components of the provisional apparatus and resection guide of the present invention while FIG. 6 shows their position in relationship to the distal end of a femur. The entire apparatus comprises the provisional component 20 described above, an intramedullary stem 32 affixable to fixation point 25 on the provisional component 20, and a combined distal/posterior augment 33 preferably temporarily affixable to the femoral contact surface 24 of provisional component 20. Alternatively, augment 33 may comprise separate distal and posterior pieces to allow greater variation and accommodate wider ranges of differences between the individual condyles of the knee. Anterior flange resection guide 30 and anterior chamfer resection guide 31 are shown in phantom. The inner surface 21a of anterior flange 21 is relieved to allow it to fit on the end of the femur 11 prior to anterior resection, as shown in FIG. 6. However, the joint surface 21b of the anterior flange 21 when the component 20 is in place will properly correspond to the location of the same joint surface of a permanent component so that action of the joint with the provisional component 20 in place will mimic joint action following implantation of the permanent component. This relationship is important since the provisional component 20 is used to test for proper alignment of the knee joint and soft tissue balance, and to establish proper tracking of the patella 9a.

As shown in FIGS. 4, 5, 6 and 7, the position of anterior resection cutting guide 30 does not coincide with the relieved inner surface 21a of anterior flange 21. Rather, the position and angle of guide 30 corresponds to the requirement for the anterior femur contacting surface of the permanent component to be implanted and its relationship to the constant reference point of the intramedullary canal. Thus, the angle of guide 30 relative to the axis of intramedullary stem 32 will preferably correspond to that of the anterior flange and intramedullary stem of the femoral components of applicant's copending application.

Augments 33 provide buildup for the resected areas of the distal and posterior condyles of the femur 11 in order to maintain the correct anatomical relationships of the knee joint between the joint surface 26 of the provisional component 20 and the corresponding surface of a tibial component 10. The size of the augments 33 is based on the resection cuts made to the femur for the particular size of permanent component to be used. Where such cuts are standardized, there will be an equally standardized set of augments. Alternatively, where the cuts are made on a case by case basis, a wider variety of augment sizes will be available. The augments 33 may be provided with the provisional component 20 or they may be those provided with the permanent component in which case they will be temporarily attachable to the provisional component so that they may be removed and permanently mounted on the permanent component prior to its implantation. As shown in FIGS. 5 and 6, the one piece augments 33 have a substantial L-shape corresponding to the interior shape of the provisional component 20 at the distal/posterior portion. As such, the augments 33 comprise a distal portion 33a and a posterior portion 33b. Alternatively, the augments may be provided as separate distal and posterior portions corresponding to portions 33a and 33b. Due to the nature of the resection of the distal femur and the fact that the extension and flexion gaps, A and B in FIGS. 2 and 3 respectively, usually are different following resection, the distal and posterior portions of the augments are usually of different thicknesses. These thicknesses are determined by the resection cuts made to the distal femur relative to the size of the femoral component to be implanted. The provisional component of this invention allows the selection of augments 33 to be tested for accuracy in establishing the extension and flexion gaps. In addition, the provisional component and the temporary placement of the augments therewith permits the establishment of the proper position of the patella 9a relative to the joint line. As shown in FIG. 2, the joint line 34 passes through the joint at a point tangential to the femoral component 9 and the tibial component 10. The position of the patella 9a relative to this line is given as C and will depend on the particular anatomical size of a knee. This position is variable by changing the augment 33 to one having a different distal thickness 33a thus altering both the extension gap A and the patella position C. Similarly, changing the augment 33 to one having a different posterior thickness 33b will alter the flexion gap B. In instances where it becomes necessary to upsize to the next size provisional component and prosthesis, appropriately sized augments will be employed to ensure that the flexion and extension gaps are properly established for even tension across the knee. In this manner an accurate relationship of the provisional component 20 to the hard and soft tissues of the knee joint may be established before the final resection of the anterior femur is performed. In addition the necessary augments 33 to be used with a permanent implant component are selected and can then be attached to the permanent implant component.

In the surgical procedure employed with this apparatus the proximal tibia is prepared by incrementally reaming the tibial intramedullary canal out to cortical bone, leaving the reamer in place as a point of reference for a tibial cutter, resecting the proximal tibia and applying provisional components for the tibial portion of the knee joint. Following this, the distal femur is prepared using the above described apparatus. Alternatively, the femur may be prepared first followed by the preparation of the tibia.

For preparation of the distal femur, the femoral intramedullary canal is first reamed incrementally to cortical bone. The canal, as stated, is the constant reference point for the resection of the distal femur. The reamer may be left in place or a provisional stem or similar intramedullary rod may be inserted on which distal and posterior cutters are mounted for resection of the distal and posterior surfaces of the femur. These cuts will be made based on the condition of the bone and on the permanent prosthesis to be implanted but will preferably be made according to a standard established by the prosthesis system being used. The individual condyles of the posterior and distal surfaces may be resected to different levels and brought up to the same level by the use of augments.

Following the posterior and distal resection, the femoral provisional component is put in place to test the positions of the selected prosthesis and the tissues of the knee joint. If the provisional stem was used as the support for the posterior and distal cutters then the provisional component may be substituted for those cutters otherwise it is preferable that the cutter support be removed from the intramedullary canal, the provisional stem attached to the provisional component and that assembly put in place. Augments may be attached as needed to establish the correct joint characteristics or a different size provisional component may be tried. Since all sizes of provisionals have the same stem/anterior flange distance and the same stem/anterior cortex angle, those characteristics and the resulting position of the anterior flange cuts will be the same regardless of the size provisional used. Once all such characteristics have been established, the provisional component and its included anterior resection guides are used for the final anterior chamfer and anterior flange cuts following which the provisional component, stem and augments are removed and the permanent implant component inserted.

The foregoing description sets forth the preferred form of the apparatus of this invention and the method for its use. However, other modifications and variations will become apparent to those having skill in the art from an examination of that description and the accompanying drawings. Therefore, other variations of the present invention may be made which fall within the scope of the appended claims even though such variations were not specifically discussed.

What is claimed is:

1. A method of knee joint arthroplasty [comprising preparing a distal femur to accept a femoral component in knee replacement surgery wherein the femoral intramedullary canal is used as the reference point for all resection cuts] comprising the steps of:

[i. incrementally reaming the intramedullary canal out to cortical bone with a reamer means;

ii. leaving said reamer means in place and attaching thereto a distal cutting guide;

iii. resetting medial and lateral distal surfaces of said femur along said distal cutting guide;

iv. replacing said distal cutting guide with a posterior cutting guide and resetting medial and lateral posterior condylar surfaces of said femur along said posterior cutting guide;]

[v]*i*. [removing said posterior cutting guide and reamer, attaching a provisional intramedullary stem] *attaching* to a provisional femoral component *to a distal femur surface what has been preliminarily resected*, *which* said provisional femoral component [including an anterior] *includes a* cutting guide formed therein and an outer surface [replicating] *that replicates* the size of a permanent femoral component[, and inserting said stem into said intramedullary canal];

[vi]*ii*. evaluating flexion/extension gaps of the knee and patella tracking relative to said provisional femoral component and establishing correct gaps and soft tissue balance of said knee relative to the anatomical size of said knee;

[vii]*iii*. resetting [an anterior surface of] said femur *surface* along said [anterior] cutting guide of said provisional femoral component; and

[viii]*iv*. removing said [provisional stem and] provisional *femoral* component and [inserting] *replacing it with* a permanent femoral component [corresponding] *that corresponds* to said provisional component.

2. The method of claim 1 wherein said provisional femoral component comprises an anterior flange, first and second posterior condylar flanges and an intermediate distal femoral joint portion, said flanges and distal femoral joint portion being formed as a single element having a continuous joint surface around its outer perimeter.

3. The method of claim 2 wherein said provisional femoral component further comprises said anterior resection cutting guide, said guide comprising means relative to said anterior flange for guiding a bone saw in resection of said anterior femoral surface.

4. The method of claim 3 wherein said guide means relative to said anterior flange comprises at least one slot formed in and through said provisional femoral component posteriorly of said anterior flange and extending inward from an edge thereof to a point adjacent a center line of said component, said slot having an angle relative to said component corresponding to that of an anterior flange of a permanent femoral knee joint prosthesis component.

5. The method of claim 2 further comprising adjusting said flexion/extension gaps and thereby the position of said provisional component by interposing provisional augment means between said component and said femur.

6. The method of claim 5 wherein said provisional augment means comprise distal and posterior portions having an angular relationship corresponding to that of said posterior condylar flanges and said intermediate distal femoral joint portion.

7. The method of claim 6 wherein said provisional augment means are temporarily interposable between said component and said femur and may be removed therefrom and permanently adhered to a permanent implant component.

8. The method of claim 1 wherein resection cuts made to said distal femur have constant angular characteristics relative to said intramedullary canal irrespective of the anatomical size of the knee on which said arthroplasty is conducted.

9. The method of claim 8 wherein resection cuts are determined by geometric constants defining the construction of a set of permanent femoral components from which said permanent component corresponding to said provisional component is selected.

10. A method of knee joint arthroplasty for revision surgery of a human knee wherein resection of a distal femur preparatory to implantation of a femoral component employs the femoral intramedullary canal as the reference point for all resection cuts, comprising:

i. removing an existing femoral component;

[ii. fitting a cutting guide means to said femur by a means extending into said femoral intramedullary canal and first resetting medial and lateral distal surfaces of said femur and medial and lateral posterior condylar surfaces of said femur;]

[iii]*ii*. [removing said cutting guide means and] fitting a provisional femoral knee component *onto* [to] said *distal* femur *surface*, said provisional component having [an anterior] *a* cutting guide means formed therein and an outer surface [replicating] *that replicates* the size of a permanent femoral component[, and wherein said provisional component comprises an intramedullary stem which is inserted into said intramedullary canal];

[iv. evaluating and adjusting flexion and extension gaps of the knee and patella tracking relative to said provisional femoral component and establishing correct gaps and soft tissue balance of said knee relative to the anatomical size of said knee followed by] *iii.* resecting [an anterior] *the* surface of said *distal* femur along said [anterior] cutting guide;

[v]*iv.* removing said provisional *femoral knee* component and inserting a permanent femoral component corresponding to said provisional component[; wherein, said anterior resection of said femur comprises an anterior flange cut and an anterior chamfer cut, said cuts having constant angular characteristics relative to said intramedullary canal irrespective of the anatomical size of the knee on which said arthroplasty is performed].

11. The method of claim 10 wherein said provisional femoral component comprises an anterior flange, first and second posterior condylar flanges and an intermediate distal femoral joint portion, said flanges and distal femoral joint portion being formed as a single element having a continuous joint surface around its outer perimeter.

12. The method of claim 11 wherein said constant angular characteristics of said anterior resection cuts correspond to and are determined by a stem/anterior flange distance and a stem/anterior cortex angle which are constant for all sizes of provisional components.

13. A method of preparing a distal femur to accept a femoral component in knee replacement surgery wherein the femoral intramedullary canal is used as the reference point for all resection cuts, the method comprising the steps of:

[i. fitting a first cutting guide means to said distal femur by a means extending into said intramedullary canal and performing a first resection of the medial and lateral distal surfaces of said femur and the medial and lateral condylar surfaces of said femur;

ii. removing said first cutting guide means;]

[iii] *i.* [providing] *fitting* a provisional *femoral* component [for connection] to [said resected] *a distal* femur [to measure the correct size of a permanent component to use with the resected femur.] *surface that has been preliminarily resected,* said provisional component including an inner surface *that is* engageable with [the] *said* resected *distal* femur *surface* and *has* an outer surface [replicating] *that replicates* the size of [the] *said* permanent *femoral* component, [and] *that includes* at least one slot extending from [the] *said provisional component* outer surface to receive a cutting tool for further resection of [the] *said* distal femur *surface* to prepare [the] *said distal* femur *surface* for connection with said permanent *femoral* component;

[iv]*ii.* fitting said provisional *femoral* component to said *further* resected *distal* femur *surface*, evaluating and adjusting flexion and extension of the knee and patella tracking relative to said provisional *femoral* component, and performing a second resection of said distal femur using said at least one slot of said provisional *femoral* component as a guide means*; and*

[v]*iii.* removing said provisional *femoral* component and insetting *in its place* a permanent *femoral* component corresponding to said provisional *femoral* component.

14. The method of claim 13 wherein said second resection comprises resection of the anterior surface of the distal femur and is performed at angles having constant characteristics relative to said intramedullary canal irrespective of the anatomical size of the knee on which said knee replacement is performed.

15. The method of claim 14 wherein said provisional component comprises an anterior flange, first and second posterior condylar flanges and an intermediate distal femoral joint portion, said flanges and distal femoral joint portion being formed as a single element having a continuous joint surface around its outer perimeter.

16. The method of claim 15 wherein said constant angular characteristics of said anterior resection cuts correspond to and are determined by a stem/anterior flange distance and a stem/anterior cortex angle which are constant for all sizes of provisional components.

17. The method of claim 15 wherein said at least one slot of said provisional component is located posteriorly of said anterior flange and extends inward from an edge thereof to a point adjacent a center line of said component, said slot having an angle relative to said component corresponding to that of an anterior flange of said femoral component.

18. The method of claim 17 wherein said provisional component comprises a further slot located posteriorly of said at least one slot and at an angle relative to said at least one slot whereby resection of said distal femur through said further slot produces a chamber on said distal femur.

* * * * *